(12) United States Patent
Roth et al.

(10) Patent No.: US 8,823,401 B2
(45) Date of Patent: Sep. 2, 2014

(54) PARTICULATE MATTER SENSOR WITH TWO PAIRS OF SENSING ELECTRODES AND METHODS OF USING SAME

(75) Inventors: Gregory T. Roth, Davison, MI (US); Lary R. Hocken, Davison, MI (US)

(73) Assignee: Delphi Technologies, Inc., Troy, MI (US)

( * ) Notice: Subject to any disclaimer, the term of this patent is extended or adjusted under 35 U.S.C. 154(b) by 183 days.

(21) Appl. No.: 13/434,977

(22) Filed: Mar. 30, 2012

(65) Prior Publication Data

US 2013/0257460 A1 Oct. 3, 2013

(51) Int. Cl.
G01R 27/08 (2006.01)

(52) U.S. Cl.
USPC ........................................................ 324/699

(58) Field of Classification Search
None
See application file for complete search history.

(56) References Cited

U.S. PATENT DOCUMENTS

| | | | |
|---|---|---|---|
| 4,656,832 A | 4/1987 | Yukihisa et al. | |
| 6,634,210 B1 | 10/2003 | Bosch | |
| 7,954,230 B2 | 6/2011 | Nelson | |
| 2008/0190173 A1* | 8/2008 | Wienand et al. | 73/28.01 |
| 2008/0282769 A1 | 11/2008 | Nelson | |
| 2008/0283398 A1 | 11/2008 | Nelson et al. | |
| 2009/0126458 A1 | 5/2009 | Fleischer et al. | |
| 2009/0139081 A1 | 6/2009 | Nelson | |
| 2009/0188300 A1* | 7/2009 | Gualtieri et al. | 73/28.01 |
| 2010/0126248 A1* | 5/2010 | Hall | 73/23.33 |
| 2010/0147052 A1 | 6/2010 | Nelson et al. | |
| 2011/0048106 A1* | 3/2011 | Zawacki et al. | 73/28.01 |

* cited by examiner

*Primary Examiner* — Melissa Koval
*Assistant Examiner* — Trung Nguyen
(74) *Attorney, Agent, or Firm* — Mark H. Svoboda

(57) ABSTRACT

A particulate matter sensor includes a first pair of sensing electrodes with a gap therebetween and a second pair of sensing electrodes with a gap therebetween. A method for determining an amount of soot on the particulate matter sensor includes determining the electrical resistance between the first pair of electrodes and the electrical resistance between the second pair of electrodes. The amount of soot deposited on the particulate matter sensor is determined based on the electrical resistance values. The time rate of change of resistance between the first pair of electrodes and the time rate of change of resistance between the second pair of electrodes are determined. The first and second rates of change are compared to each other and to threshold values, and the determination of soot amount may be modified depending on the results of these comparisons.

10 Claims, 6 Drawing Sheets

US 8,823,401 B2

PARTICULATE MATTER SENSOR WITH TWO PAIRS OF SENSING ELECTRODES AND METHODS OF USING SAME

BACKGROUND OF THE INVENTION

Soot sensors, also known as particulate matter (PM) sensors, may be used in vehicles having diesel engines. A particulate matter sensor may be located upstream from a diesel particulate filter (DPF), where the sensor is exposed to exhaust flow from the engine having soot particles entrained in the exhaust gas. Alternatively, a particulate matter sensor may be located in a gas stream downstream from a diesel particulate filter (DPF), where the sensor is used to monitor the proper operation of the particulate filter.

A known method of sensing soot uses a particulate matter sensor having two electrodes that are spaced from one another. In the absence of soot, there is very low electrical conductivity (high electrical resistance) between the electrodes. As soot accumulates on the surface of the sensor, soot particles act to bridge the gap between the electrodes. Because the soot particles are electrically conductive the conductivity between the electrodes increases, and this change in conductivity can be related to the amount of soot in the gas stream. Sensors that operate according to this principle are disclosed in U.S. patent application Ser. No. 11/749,262 published as US Patent Application Publication 2008/0283398, U.S. patent application Ser. No. 11/750,883 published as US Patent Application Publication 2008/0282769, and U.S. patent application Ser. No. 11/998,238 published as US Patent Application Publication 2009/0139081, the contents of all of which are hereby incorporated by reference in their entirety.

Government regulations require that the vehicle system must be able to detect when a DPF has failed. The particulate matter sensor algorithm determines this by measuring the rate of soot that passes the sensing element. The particulate matter sensing environment may contain sources of significant noise. These noise sources are primarily voltage-based noise (i.e. EMI or conducted ground noise) and soot based noise (i.e. large particulate matter particles or agglomerate particulate matter loss). The noise on the particulate matter sensor signal can interfere with the ability to detect when a DPF has failed.

Accordingly, the inventors herein have recognized a need for an improved sensing system having a particulate matter sensor that reduces and/or eliminates the foregoing deficiencies.

BRIEF SUMMARY OF THE INVENTION

A particulate matter sensor includes a first pair of sensing electrodes with a gap therebetween and a second pair of sensing electrodes with a gap therebetween. A method for determining an amount of soot on the particulate matter sensor includes determining the electrical resistance between the first pair of electrodes and the electrical resistance between the second pair of electrodes. The amount of soot deposited on the particulate matter sensor is determined based on the electrical resistance values. The time rate of change of resistance between the first pair of electrodes and the time rate of change of resistance between the second pair of electrodes are determined. The first and second rates of change are compared to each other and to threshold values, and the determination of soot amount may be modified depending on the results of these comparisons.

DETAILED DESCRIPTION OF THE INVENTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "left", "right", "horizontal", "vertical", "bottom", and "top" are used herein, unless otherwise noted, merely for convenience of description, and are not limited to any one position or spatial orientation. Finally, unless defined otherwise, technical and scientific terms used herein have the same meaning as is commonly understood by one of skill in the art to which this invention belongs.

In describing and claiming algorithms according to the invention, letters and naming conventions are arbitrarily employed to represent numerical values (e.g., $R_{pullup1}$, $KLargePM\_Delta\_ohms$). These naming conventions are used solely to enhance the readability of the description of the invention, and are not intended to have any functional significance whatsoever. The representation of these numerical values is intended to be precisely the same as if, for example completely arbitrary descriptions (e.g., $R_1$, $R_2$, $K_1$, $K_2$) had been used. Additionally, it should be noted that in the practice of the invention, measurements of resistance between the electrodes may be made by applying a known current across the electrodes, measuring the voltage differential between the electrodes and calculating the resistance using Ohm's law, as is well-known in the art. It would of course be possible to simply use the voltage values in place of resistance values in the algorithm of the invention by converting the various resistance constants and equations to voltage, and such alternative embodiments are considered to be within the scope of the invention.

Figure 1:
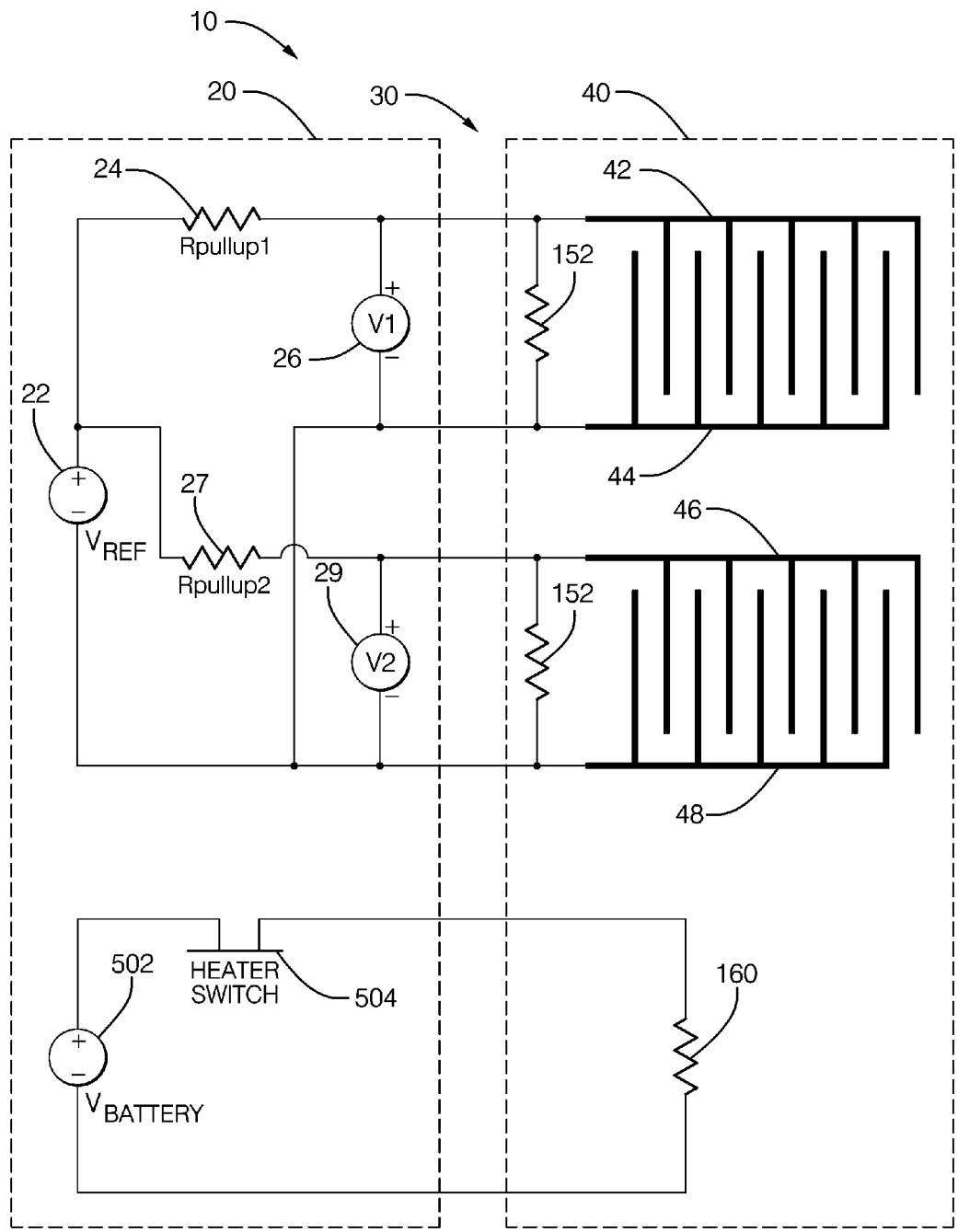
FIG. 1 is an electrical schematic of a particulate matter sensing system incorporating aspects of the invention.

FIG. 1 is an electrical schematic of a portion of a particulate matter sensing system 10. The system 10 may be generally considered to be partitioned as indicated into a controller portion 20, a wiring harness portion 30, and a sensing element portion 40. The controller portion 20 comprises a means for measuring the impedance of circuits connected thereto. In the exemplary controller portion 20 in FIG. 1, the impedance measurement means includes a reference voltage source 22 that provides a voltage value $V_{ref}$, a pull-up resistor 24 having a resistance value $R_{pullup1}$, and a voltage measurement means 26. The exemplary controller portion 20 in FIG. 1 further includes a pull-up resistor 27 having a resistance value $R_{pullup2}$, and a voltage measurement means 29. While voltage source 22 is depicted in FIG. 1 as a DC source with a given polarity, it will be appreciated that voltage source 22 can alternatively be an AC source, a DC source having opposite polarity from what is depicted, or a source providing both an AC and a DC voltage component, without departing from the inventive concept described herein. In the exemplary embodiment of FIG. 1, the controller portion 20 electrically interfaces to the sensing element portion 40 by means of wiring harness portion 30.

The sensing element portion 40 comprises a first electrode pair that includes a first electrode 42 and a second electrode 44. FIG. 1 also includes an optional bias resistor 152 connected between the first electrode 42 and the second electrode 44. The function of the bias resistor 152 is described in detail in commonly owned U.S. patent application Ser. No. 12/947,867 filed Nov. 17, 2010 and titled SELF DIAGNOSTICS OF A PARTICULATE MATTER SENSOR, the entire contents of which are hereby incorporated by reference. For the following discussion, the bias resistor 152 will be ignored, i.e. treated as an open circuit.

As formed on the sensing element, the first electrode 42 is electrically isolated from the second electrode 44, so that the impedance between the first pair of electrodes appears electrically as an open circuit in the absence of particulate matter. In the absence of particulate matter, the voltage measured by measurement means 26 will be essentially equal to $V_{ref}$, the voltage provided by reference voltage source 22. The first electrode 42 and second electrode 44 are preferably shaped in the form of interdigitized fingers with a small gap therebetween. In operation, particulate matter that is deposited on the sensing element so as to bridge the gap between the electrodes 42, 44 can be detected because the particulate matter forms a conductive path bridging the normally open circuit between the electrodes 42, 44.

If the resistance of the particulate matter bridging the first pair of electrodes is assigned the value $R_1$, the voltage measured by measurement means 26 (ignoring the effects of the bias resistor 152) will be:

$$V_{measured1} = V_{ref} \frac{R_1}{R_{pullup1} + R_1}$$

As particulate matter accumulates between first electrode 42 and second electrode 44, the resistance $R_1$ will decrease, and the voltage $V_{measured1}$ at measurement means 26 will decrease from the maximum value of $V_{ref}$. The controller portion can thereby determine the impedance between the electrodes 42, 44 as a function of the voltage measured by measurement means 26.

The sensing element portion 40 further comprises a second electrode pair that includes a third electrode 46 and a fourth electrode 48. FIG. 1 also includes an optional bias resistor 152 connected between the third electrode 46 and the fourth electrode 48. For the following discussion, the bias resistor 152 will be ignored, i.e. treated as an open circuit.

As formed on the sensing element, the third electrode 46 is electrically isolated from the fourth electrode 48, so that the impedance between the second pair of electrodes appears electrically as an open circuit in the absence of particulate matter. In the absence of particulate matter, the voltage measured by measurement means 29 will be essentially equal to $V_{ref}$, the voltage provided by voltage source 22.

The third electrode 46 and fourth electrode 48 are preferably shaped in the form of interdigitized fingers with a small gap therebetween. In operation, particulate matter that is deposited on the sensing element so as to bridge the gap between the electrodes 46, 48 can be detected because the particulate matter forms a conductive path bridging the normally open circuit between the electrodes 46, 48. If the resistance of the particulate matter bridging the second pair of electrodes is assigned the value $R_2$, the voltage measured by measurement means 29 will be:

$$V_{measured2} = V_{ref} \frac{R_2}{R_{pullup2} + R_2}$$

As particulate matter accumulates between third electrode 46 and fourth electrode 48, the resistance $R_2$ will decrease, and the voltage $V_{measured2}$ at measurement means 29 will decrease from the maximum value of $V_{ref}$. The controller portion can thereby determine the impedance between the electrodes 46, 48 as a function of the voltage measured by measurement means 29.

The sensing element 40 of FIG. 1 additionally includes a heater resistance 160, electrically connected to a voltage source 502 through a heater switch 504. The heater 160 is controllable to raise the temperature in the vicinity of the electrodes 42, 44, 46, and 48 on the sensing element 40. Raising the temperature sufficiently will result in the particulate matter being removed from the surface of the sensing element, thereby restoring the resistance of the area between the sensing electrodes 42, 44, 46, and 48 to a high resistance or essentially open circuit condition.

The wiring harness portion 30 of system 10 includes a total of six conductors: two conductors providing connection to the first pair of sensing electrodes 42, 44; two conductors providing connection to the second pair of sensing electrodes 46, 48; and two conductors providing connection to the heater 160.

Figure 2:
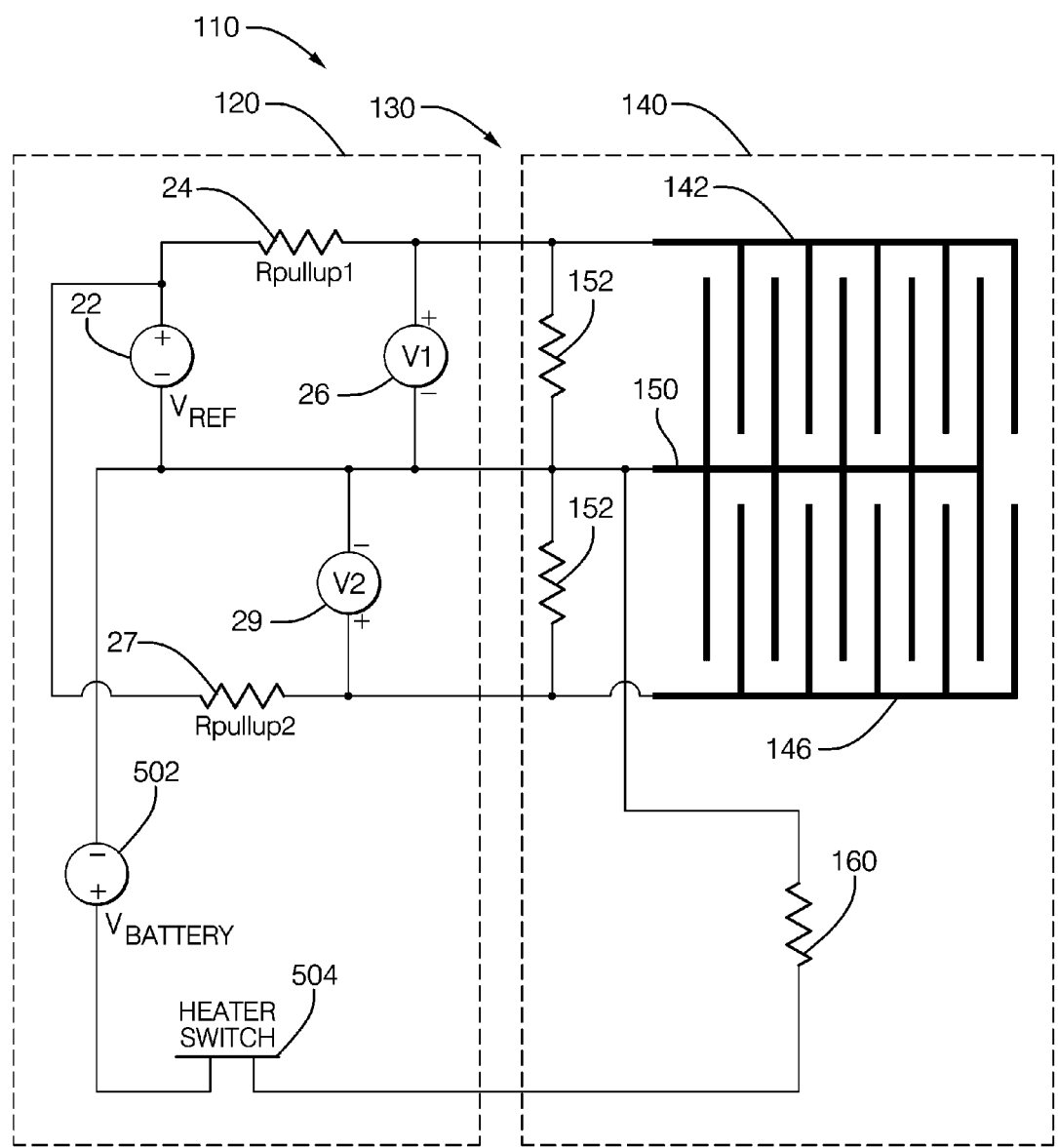
FIG. 2 is an electrical schematic of an alternative particulate matter system incorporating aspects of the invention.

FIG. 2 is an electrical schematic of an alternative particulate matter sensing system 110. The sensing element 140 of FIG. 2 differs from the sensing element 40 of FIG. 1 in that the electrodes 44 and 48 in the sensing element 40 of FIG. 1 are combined into a single electrode 150 in sensing element 140. In FIG. 2, the first pair of electrodes comprises electrodes 142 and 150, and the second pair of electrodes comprises electrodes 146 and 150. By providing a sensing element 140 as shown in FIG. 2, connection means need only be provided for three interconnections in the wire harness portion 130 between controller 120 and the electrodes on sensing element 140, compared to the four interconnections required in the wire harness portion 30 between controller 20 and the electrodes on sensing element 40 in FIG. 1. FIG. 2 also includes an optional bias resistor 152 connected between the first pair of electrodes 142, 150, and another optional bias resistor 152 connected between the second pair of electrodes 146, 150. Again treating the bias resistors 152 as open circuits, it will be appreciated that the foregoing equations relating voltages and resistances presented with respect to FIG. 1 also apply to the configuration of FIG. 2.

Additionally, the sensing element 140 shown in FIG. 2 shows one of the conductors leading to the heater 160 connected to the conductor leading to the common electrode 150. It will be appreciated that the system 110 diagrammed in FIG. 2 only requires four conductors in its wiring harness portion 130 (compared to the six conductors in wiring harness portion 30 in FIG. 1): one conductor to each of electrodes 142 and 146; one conductor to one end of heater 160, and one conductor common to the other end of heater 160 and to shared electrode 150.

While it may be convenient to configure the particulate matter sensor as a part of a voltage divider circuit and to measure the voltage across the sensor as depicted in FIGS. 1 and 2, one skilled in the art may employ other circuit configurations or measure other electrical characteristics associated with the sensor. Depending on the circuit configuration, an electrical characteristic such as a voltage across the sensor, a voltage across a circuit element in electrical connection with the sensor, a current through the sensor, electrical conductance, a current through a circuit element in electrical connection with the sensor, or the like may be used to derive information related to the effective impedance of the sensor.

Figure 3:
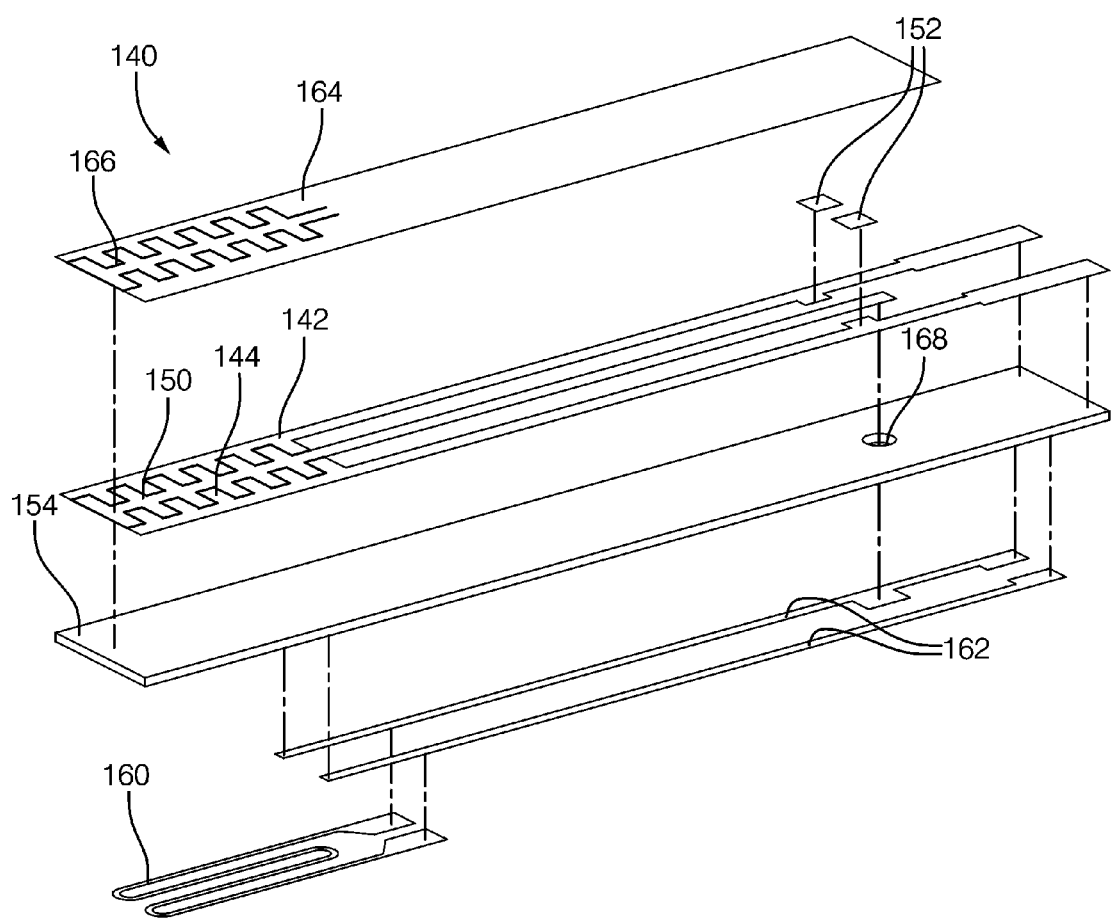
FIG. 3 is an exploded view of a sensing element as found in the particulate matter sensing system of FIG. 2.

FIG. 3 is an exploded perspective view of the sensing element 140 of FIG. 2. The sensing element 140 includes an electrically insulating substrate 154. While shown as a single layer, it will be appreciated that substrate 154 may be formed by laminating together a plurality of layers. Conductive material disposed on one surface of substrate 154 is patterned to form electrodes 142, 146, and 150. A protective layer 164 may also be included to protect the conductive material that forms electrodes 142, 146, and 150. The protective layer 164 includes an open area 166 exposing the gap between the electrodes 142, 146, and 150, thereby allowing particulate matter to bridge the electrodes 142, 146, and 150.

A particulate matter sensor may also include a heating means 160 that is controllable to raise the temperature in the vicinity of the electrodes 142, 146, and 150 on the sensing element 140. Raising the temperature sufficiently will result in the particulate matter being removed from the surface of the sensing element, thereby restoring the resistance of the area between the sensing electrodes 142, 146, and 150 to a high resistance or essentially open circuit condition. The sensing element 140 depicted in FIG. 3 includes a heater 160 and heater leads 162, on the opposite surface of the substrate 154 from the electrodes 142, 146. As shown in FIG. 3, an electrical connection may be made connecting one of the heater leads 162 to the electrode 150 by means of the via hole 168 defined in the substrate 154. The heater 160 is positioned to allow the heater 160 to clean the particulate matter from the vicinity of the electrodes 142, 146, and 150 when the heater 160 is electrically powered by supplying current through heater leads 162. An additional substrate layer, not shown in FIG. 3, may be included on the opposite side of heater 160 from the substrate layer 154 in FIG. 3, thereby placing the heater 160 on an inner layer of a multi-layer sensor. The process of heating the sensing element 140 to clean the particulate matter from the vicinity of the electrodes is known as regeneration.

It will be appreciated that the impedance indicated by a particulate matter sensor will have a maximum value in the absence of particulate matter on the sensor. As particulate matter accumulates on the sensor, the impedance will decrease from this maximum value, and the change in impedance can be detected as a change in voltage measured by the measurement means 26, 29. The rate of change of the sensor impedance, and hence the rate of change of the measured voltage, is related to the rate of soot accumulation on the sensor. A large soot particle landing on the sensor may cause a sudden step decrease in sensor resistance, and an agglomeration of soot particles blowing off the sensor may cause a sudden step increase in sensor resistance. These large step changes make it difficult to make a determination of particulate matter accumulation that is meaningful, for example, in determining the integrity of a diesel particulate filter.

In an aspect of the invention, a method is presented which uses the impedance information for the first pair of electrodes 142, 150 and from the second pair of electrodes 146, 150 of a sensing element 140 to make an improved determination of particulate matter accumulation on the sensing element 140. A flow chart of an exemplary method is presented in FIG. 4.

Figure 4A:
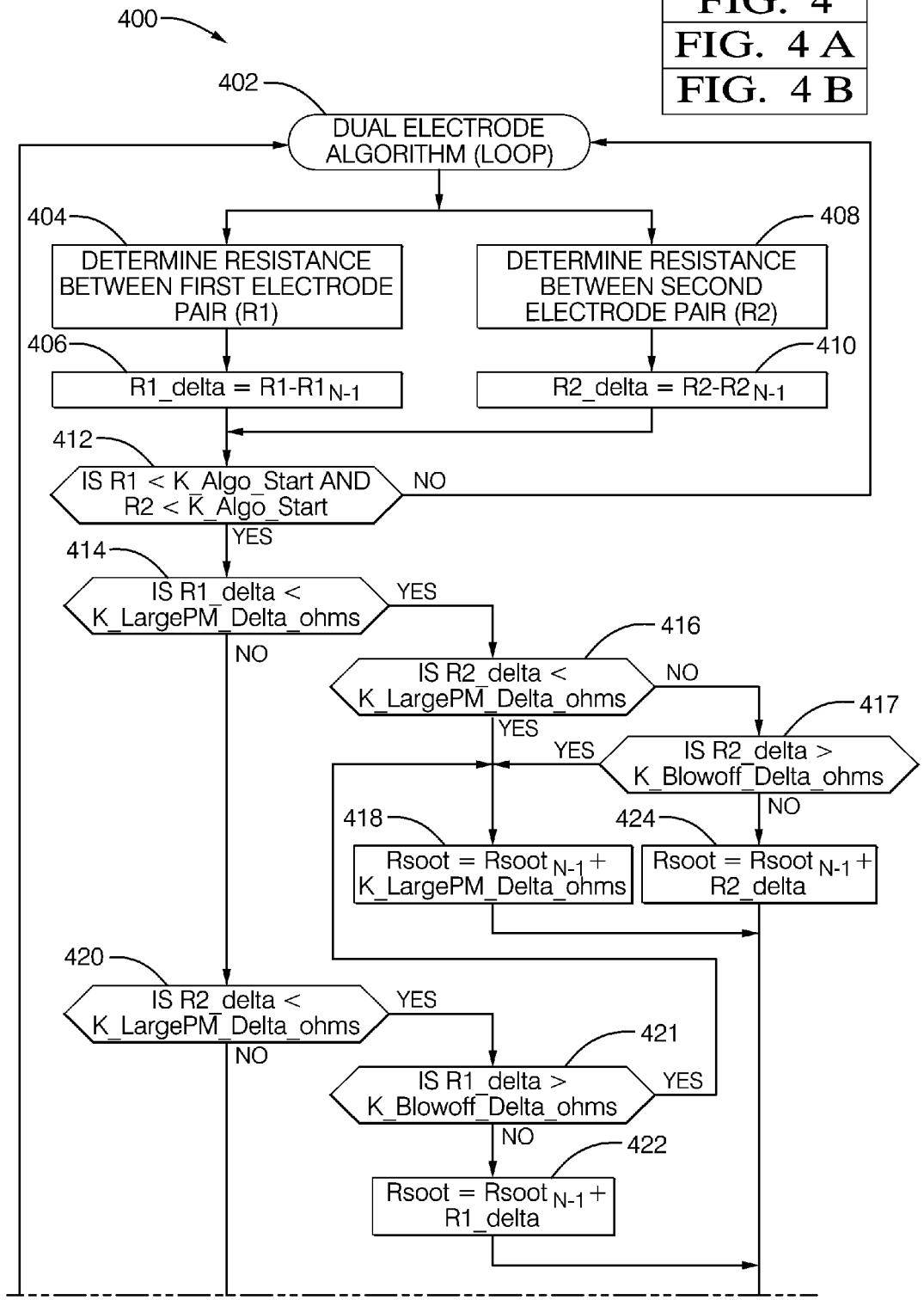
FIG. 4 is a flow chart of an exemplary embodiment of a particulate matter detection method incorporating aspects of the invention.
Figure 4:
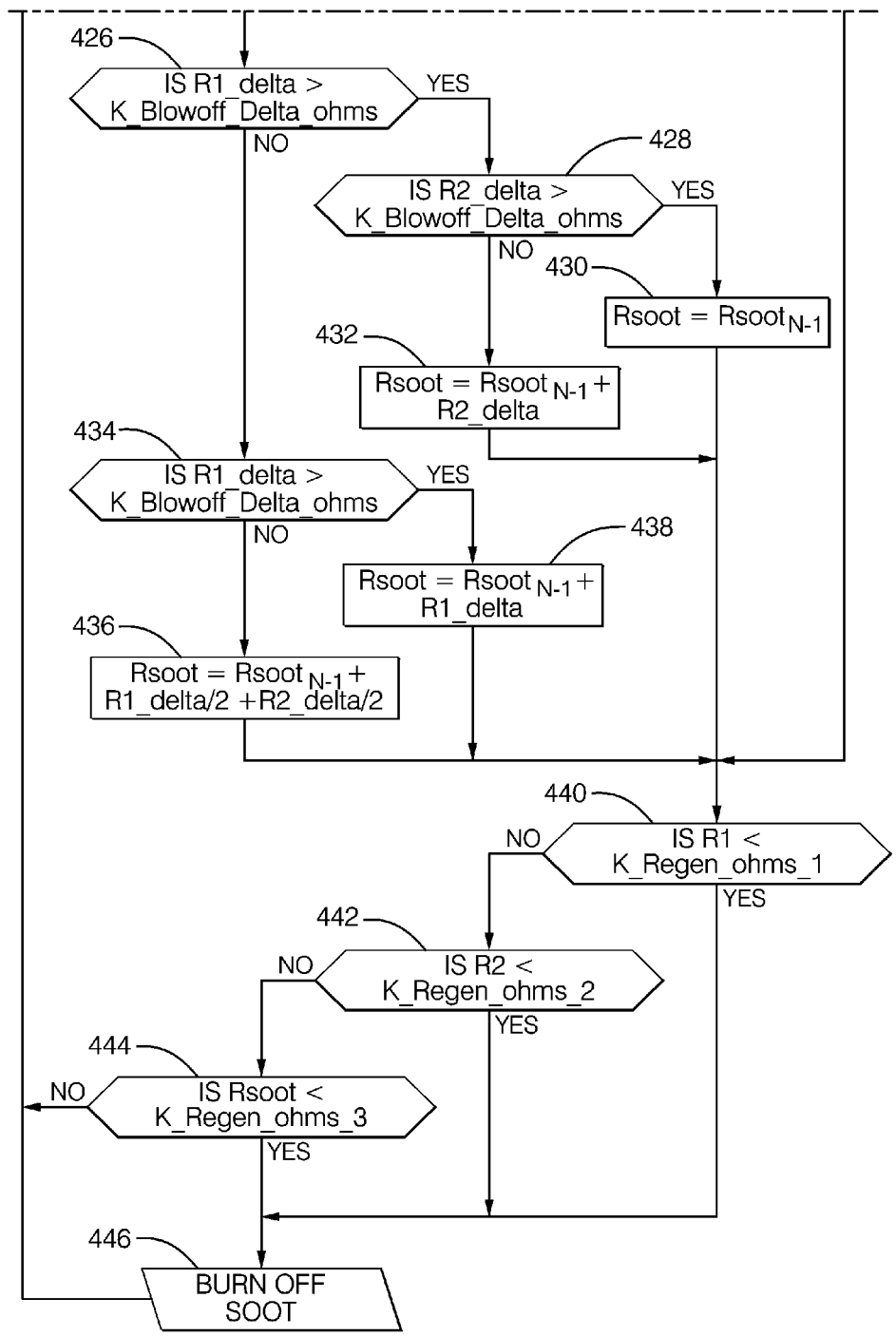

Referring now to FIG. 4, a method 400, starting at node 402, includes determining R1 in step 404, where R1 represents the resistance between the first pair of electrodes 142, 150. After R1 is determined in step 404, R1_delta is determined in step 406 as the difference between the current value of R1 and the previously determined value of R1. Similarly R2 is determined in step 408, where R2 represents the resistance between the second pair of electrodes 146, 150. After R2 is determined in step 408, R2_delta is determined in step 410 as the difference between the current value of R2 and the previously determined value of R2.

In step 412, each of the determined resistances R1 and R2 are compared to a predetermined threshold value identified as K_Algo_Start. If both resistances R1 and R2 are below K_Algo_Start, this is an indication that sufficient soot has accumulated between both pairs of electrodes to continue with the remainder of the method and the method proceeds to step 414. If either R1 or R2 is above K_Algo_Start, indicating an insufficient amount of soot accumulation between the corresponding electrode pair, the method returns to node 402 and loops through the previously described steps until sufficient soot is detected in step 412.

After a determination has been made in step 412 that sufficient soot has accumulated between both pairs of electrodes, i.e. that R1 and R2 are both less than K_Algo_Start, the method proceeds to step 414, which tests to see if R1_delta is less than (i.e. more negative than) a predetermined threshold value K_LargePM_Delta_ohms. A value of R1_delta that is more negative than the threshold value K_LargePM_Delta_ohms is an indication that a large particle of soot has deposited between the first pair of electrodes.

If a large particle is sensed between the first electrode pair in step 414, the algorithm proceeds to step 416. Step 416 tests to see if R2_delta is more negative than the threshold value K_LargePM_Delta_ohms, which would indicate that a large particle of soot has deposited between the second pair of electrodes.

If step 416 determines that a large particle has also been deposited between the second pair of electrodes in addition to a large particle being deposited between the first pair of electrodes, the algorithm proceeds to step 418, which will be discussed below. If the result of the test in step 414 is that R1_delta is not more negative than the predetermined threshold value K_LargePM_Delta_ohms, i.e. that a large particle was not detected between the first pair of electrodes, the algorithm proceeds to step 420. Step 420 tests to see if R2_delta is more negative than the threshold value K_LargePM_Delta_ohms, which would indicate that a large particle of soot has deposited between the second pair of electrodes. If the results of the test in step 420 is that R2_delta is more negative than the predetermined threshold value K_LargePM_Delta_ohms, i.e. that a large particle was detected between the second pair of electrodes, the algorithm proceeds to step 421.

If soot particles are removed from the sensor 140 between a pair of electrodes, the resistance between that pair of electrodes will increase. This removal may be the caused by several means, for example by soot being blown off the sensor by exhaust gas passing over the surface of the sensor 140, by soot being removed from the surface of the sensor by a collision with another soot particle, or by soot being shaken from the surface of the sensor due to vibration. The terms "blow off" and "blown off" will be used herein to refer to the removal of soot from the surface of the sensor, regardless of the actual mechanism responsible for the soot removal.

In step 421, a test is performed to determine if R1_delta is greater (more positive) than a predetermined constant K_Blowoff_Delta_ohms, i.e. to determine if a significant quantity of soot was blown off from the sensor between the first pair of electrodes. If it is determined in step 421 that significant blow off occurred between the first pair of electrodes, the algorithm proceeds to step 418. If it is determined in step 421 that significant blow off did not occur between the first pair of electrodes, the algorithm proceeds to step 422.

In step 422, which is executed only if it is determined that a large particle was not deposited between the first pair of electrodes, that a large particle was deposited between the second pair of electrodes, and that blow off did not occur between the first pair of electrodes, the value of variable Rsoot is set to the sum of $Rsoot_{N-1}$ (the previous value of Rsoot) and R1_delta, thereby effectively ignoring the large resistance change resulting from the large particle between the second pair of electrodes. The algorithm then proceeds from step 422 to step 440, which will be discussed below.

If the results of the test in step 416 (which is entered only if step 414 determines the presence of a large particle between the first pair of electrodes) is that R2_delta is not more negative than the predetermined threshold value K_LargePM_Delta_ohms, i.e. that a large particle was not detected between the second pair of electrodes, the algorithm proceeds to step 417. In step 417, a test is performed to determine if R2_delta is greater (more positive) than a predetermined constant K_Blowoff_Delta_ohms, i.e. to determine if a significant quantity of soot was blown off from the sensor between the second pair of electrodes. If it is determined in step 417 that significant blow off occurred between the second pair of electrodes, the algorithm proceeds to step 418. If it is determined in step 417 that significant blow off did not occur between the second pair of electrodes, the algorithm proceeds to step 424 which will be discussed below.

Step 418 is executed if it is determined that large particles have essentially simultaneously been deposited between both electrode pairs, or if it is determined that large particles have been deposited between one electrode pair and blow off has occurred between the other electrode pair. In step 418, the value of variable Rsoot, which is corresponds to the total amount of soot accumulation on the sensor, is set to the sum of $Rsoot_{N-1}$ (the previous value of Rsoot) and a predetermined constant K_LargePM_Delta_ohms. In the case where one electrode pair indicates a large particle has been deposited and the other electrode pair indicates a blow off condition, the large particle event is given precedence and the blow off is essentially ignored. The algorithm then proceeds from step 418 to step 440, which will be discussed below.

In step 424, which is executed only if it is determined that a large particle was deposited between the first pair of electrodes, a large particle was not deposited between the second pair of electrodes, and blow off did not occur between the second pair of electrodes, the value of variable Rsoot is set to the sum of $Rsoot_{N-1}$ (the previous value of Rsoot) and R2_delta, thereby effectively ignoring the large resistance change resulting from the large particle between the first pair of electrodes. The algorithm then proceeds from step 424 to step 440, which will be discussed below.

Still referring to FIG. 4, if the results of the test in step 420 is that R2_delta is not more negative than the predetermined threshold value K_LargePM_Delta_ohms, i.e. that a large particle was not detected between the second pair of electrodes, the algorithm proceeds to step 426. For the algorithm to reach step 426, the logical results of the tests in both steps 414 and 420 must be false, i.e. no large particles are detected between either the first electrode pair or the second electrode pair.

If soot particles blow off the sensor between a pair of electrodes, the resistance between that pair of electrodes will increase. In step 426, a test is performed to determine if R1_delta is greater (more positive) than a predetermined constant K_Blowoff_Delta_ohms, i.e. to determine if a significant quantity of soot was blown off from the sensor between the first pair of electrodes.

If it is determined in step 426 that significant blow off occurred between the first pair of electrodes, the algorithm proceeds to step 428 where a similar test is performed for the resistance change between the second pair of electrodes. In step 428, a test is performed to determine if R2_delta is greater (more positive) than the predetermined constant K_Blowoff_Delta_ohms, i.e. to determine if a significant quantity of soot was blown off from the sensor between the second pair of electrodes. If it is determined in step 428 that significant blow off also occurred between the second pair of electrodes, the algorithm proceeds to step 430.

The method reaches step 430 only if it was determined in steps 426 and 428 that blow off occurred both between the first pair of electrodes and between the second pair of electrodes. In this event, step 430 maintains the value of Rsoot at the same value, $Rsoot_{N-1}$, that Rsoot had the previous time through the method, effectively ignoring the simultaneous blow off events between the two electrode pairs. The soot that was previously on the sensor that is detected as blowing off the sensor is thereby counted as true soot that was present in the exhaust gas; the blowing-off of that soot does not undo its existence. The algorithm then proceeds from step 430 to step 440, which will be discussed below.

If it is determined in step 428 that R2_delta is not greater than the predetermined constant K_Blowoff_Delta_ohms, i.e. that blow off did not occur between the second electrode pair, the method proceeds to step 432. In step 432, which is executed only if it is determined that blow off occurred between the first pair of electrodes but that blow off did not occur between the second pair of electrodes, the value of variable Rsoot is set to the sum of $Rsoot_{N-1}$ (the previous value of Rsoot) and R2_delta, thereby effectively ignoring the large resistance change resulting from the blow off between the first pair of electrodes. The algorithm then proceeds from step 432 to step 440, which will be discussed below.

If it is determined in step 426 that no significant blow off occurred between the first pair of electrodes, the algorithm proceeds to step 434 where a similar test is performed for the resistance change between the second pair of electrodes. In step 434, a test is performed to determine if R2_delta is greater (more positive) than the predetermined constant K_Blowoff_Delta_ohms, i.e. to determine if a significant quantity of soot was blown off from the sensor between the second pair of electrodes.

If it is determined in step 434 that significant blow off occurred between the second pair of electrodes, the algorithm proceeds to step 438. In step 438, which is executed only if it is determined that blow off did not occur between the first pair of electrodes but that blow off occurred between the second pair of electrodes, the value of variable Rsoot is set to the sum of $Rsoot_{N-1}$ (the previous value of Rsoot) and R1_delta, thereby effectively ignoring the large resistance change resulting from the blow off between the second pair of electrodes. The algorithm then proceeds from step 438 to step 440, which will be discussed below.

Continuing to refer to FIG. 4, if it is determined in step 434 that no significant blow off occurred between the second pair of electrodes, the algorithm proceeds to step 436. In order to reach step 436, all of the previous tests in the method must have determined that no large particles were detected and that no blow off was detected either between the first pair of electrodes or between the second pair of electrodes. In this case, with both R1_delta and R2_delta falling into "normal" ranges, the new value of Rsoot is calculated in step 436 as the sum of the previous value of Rsoot and the average of R1_delta and R2_delta. The method then proceeds from step 436 to step 440.

Each of the steps where a new value of Rsoot is calculated, namely steps 418, 422, 424, 430, 432, 436, and 438, proceeds to step 440. As shown in FIG. 4, method steps 440, 442, and 444 compare the earlier-determined resistance values R1, R2, and Rsoot to predetermined threshold values K_Regen_ohms_1, K_Regen_ohms_2, and K_Regen_ohms_3 respectively. If any of the resistance values R1, R2, or Rsoot is lower than its respective threshold value, this is indicative of enough soot deposited on the sensor to require a regeneration, and the method proceeds to step 446. In step 446, the heater 160 is energized to heat the sensor 140 sufficiently to clean the accumulated soot from the sensor. The method proceeds from step 446 to step 402, and the above-described process is repeated after the regeneration is completed.

If none of steps 440, 442, and 444 call for the sensor to be regenerated, the method proceeds from step 444 to step 402, and the above-described process is repeated.

Figure 5:
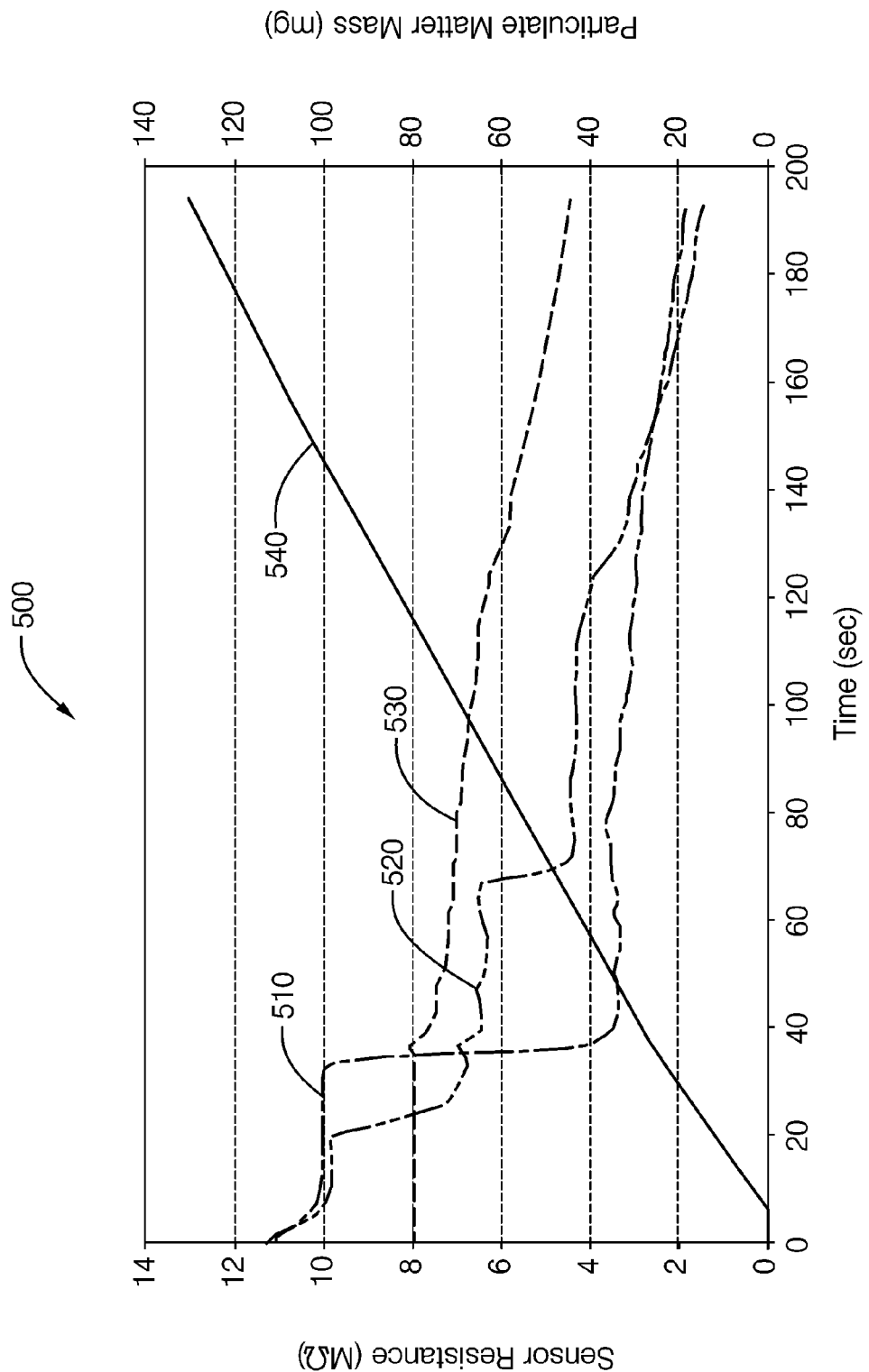
FIG. 5 is a chart illustrating signals that may be observed in a particulate matter detection system incorporating aspects of the invention.

It will be appreciated that the tests performed on the resistance differences R1_delta and R2_delta in the method shown in FIG. 4, e.g. steps 414, 416, 420, 426, 428, and 434, result in each of the resistance differences R1_delta and R2_delta being categorized as indicating either "large particle detected" (sufficiently large negative change in resistance), "blow off detected" (sufficiently large positive change in resistance), or "normal" (neither large particle nor blow off detected). With each of the two electrode pairs having three possible determinations, the method diagrammed in FIG. 4 results in adjustments to the calculated value of Rsoot that can be summarized as shown in Table 1:

electrodes and between a second pair of electrodes. The simulation includes random occurrences of large particles being deposited between either pair of electrodes, as well as including random occurrences of particle blow off occurring between either pair of electrodes. Trace 510 in FIG. 5 represents the resistance between the first pair of electrodes as a function of time, and trace 520 represents the resistance between the second pair of electrodes as a function of time. Trace 530 represents the effective soot resistance Rsoot calculated using the method depicted in the flow chart of FIG. 4, plotted as a function of time. Traces 510, 520, and 530 are all plotted against the "Sensor Resistance (MΩ)" y-axis on the left side of the chart 500. In this simulation, each of the bias resistors 152 connected across each electrode pair as discussed earlier was set to a value of 11 MΩ. Trace 540 represents the simulated total particulate matter mass deposited on the simulated sensing element as a function of time. Trace 540 is plotted against the "Particulate Matter Mass (mg) y-axis on the right side of the chart 500.

In the simulation results presented in chart 500, the calibration settings referred to in the flow chart of FIG. 4 were set to the values given in Table 2:

TABLE 2

| Variable name | Value (MΩ) |
|---|---|
| K_LargePM_Delta_ohms | −0.1 |
| K_Blowoff_Delta_ohms | 0.01 |
| K_Regen_ohms_1 | 0.5 |
| K_Regen_ohms_2 | 0.5 |
| K_Regen_ohms_3 | 1.5 |
| K_Algo_Start | 8 |

It will be appreciated that, while the total particulate matter mass increases uniformly, as shown by trace 540, the random nature of particle distribution on the sensing element results in large transients in resistance measured between the first pair of electrodes as shown by trace 510 as well as large transients in resistance measured between the second pair of

TABLE 1

| | | Soot delta between first pair of electrodes (R1_delta) | | |
|---|---|---|---|---|
| | | "Large particle" | "Normal" | "Blow off" |
| Soot delta between second pair of electrodes (R2_delta) | "Large particle" | Rsoot = Rsoot$_{N-1}$ + K_LargePM_Delta_ohms | Rsoot = Rsoot$_{N-1}$ + R1_delta | Rsoot = Rsoot$_{N-1}$ + K_LargePM_Delta_ohms |
| | "Normal" | Rsoot = Rsoot$_{N-1}$ + R2_delta | Rsoot = Rsoot$_{N-1}$ + R1_delta/2 + R2_delta/2 | Rsoot = Rsoot$_{N-1}$ + R2_delta |
| | "Blow off" | Rsoot = Rsoot$_{N-1}$ + K_LargePM_Delta_ohms | Rsoot = Rsoot$_{N-1}$ + R1_delta | Rsoot = Rsoot$_{N-1}$ |

It will be appreciated by a skilled practitioner that the exemplary method steps shown in FIG. 4 may be modified, performed in different order, etc., and still produce the results summarized in Table 1. It should be noted that the calculations for the effective soot resistance Rsoot in FIG. 4 and in Table 1 are exemplary calculations, and that the scope of the invention is not limited to these specific calculations.

Referring to FIG. 5, a chart 500 is presented that depicts signals that may be observed in a particulate matter sensing system incorporating aspects of the present invention. More specifically, FIG. 5 represents the results of a simulation in which particulate matter is deposited between a first pair of electrodes as shown by trace 520. Applying the method 400 diagrammed in FIG. 4 to the resistances determined between each individual pair of electrodes, the effective soot resistance Rsoot as shown by trace 530 exhibits the ability to reject the large transients caused by large particles and by blow off events.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but rather by the claims which follow.

The invention claimed is:

1. A method for determining an amount of soot accumulation on a soot sensor comprising a first pair of electrodes having a first gap therebetween and a second pair of electrodes having a second gap therebetween, the method comprising the steps of:
   determining the electrical resistance between the first pair of electrodes and the electrical resistance between the second pair of electrodes;
   determining a time rate of change of the electrical resistance between the first pair of electrodes and a time rate of change of the electrical resistance between the second pair of electrodes;
   determining an effective soot resistance based on the electrical resistance between the first pair of electrodes, the electrical resistance between the second pair of electrodes, the time rate of change of the electrical resistance between the first pair of electrodes, and the time rate of change of the electrical resistance between the second pair of electrodes.

2. A method for determining an amount of soot accumulation on a soot sensor comprising a first pair of electrodes having a first gap therebetween and a second pair of electrodes having a second gap therebetween, the method comprising the steps of:
   determining the electrical resistance between the first pair of electrodes and the electrical resistance between the second pair of electrodes;
   determining a time rate of change of the electrical resistance between the first pair of electrodes and a time rate of change of the electrical resistance between the second pair of electrodes;
   determining an effective soot resistance based on the electrical resistance between the first pair of electrodes, the electrical resistance between the second pair of electrodes, the time rate of change of the electrical resistance between the first pair of electrodes, and the time rate of change of the electrical resistance between the second pair of electrodes;
   wherein the step of determining an effective soot resistance includes the step of:
   comparing the time rate of change of the electrical resistance between the first pair of electrodes and the time rate of change of the electrical resistance between the second pair of electrodes to a first predetermined delta threshold value and to a second predetermined delta threshold value.

3. The method according to claim 2 wherein the step of determining an effective soot resistance includes the step of:
   if neither the time rate of change of the electrical resistance between the first pair of electrodes nor the time rate of change of the electrical resistance between the second pair of electrodes is more negative than the first predetermined delta threshold value,
   and if neither the time rate of change of the electrical resistance between the first pair of electrodes nor the time rate of change of the electrical resistance between the second pair of electrodes is more positive than a second predetermined threshold value,
   estimating the effective soot resistance as the previously estimated effective soot resistance modified by the average of the time rate of change of resistance between the first pair of electrodes and the time rate of change of resistance between the second pair of electrodes.

4. The method according to claim 2 wherein the step of determining an effective soot resistance includes the step of:
   if both the time rate of change of the electrical resistance between the first pair of electrodes and the time rate of change of the electrical resistance between the second pair of electrodes are more negative than the first predetermined delta threshold value,
   or if the time rate of change of the electrical resistance between the first pair of electrodes is more negative than the first predetermined delta threshold value and the time rate of change of the electrical resistance between the second pair of electrodes is more positive than the second predetermined delta threshold value,
   or if the time rate of change of the electrical resistance between the second pair of electrodes is more negative than the first predetermined delta threshold value and the time rate of change of the electrical resistance between the first pair of electrodes is more positive than the second predetermined delta threshold value,
   estimating the effective soot resistance as the previously estimated effective soot resistance modified by a first predetermined limit value.

5. The method according to claim 2 wherein the step of determining an effective soot resistance includes the step of:
   if the time rate of change of the electrical resistance between the one pair of electrodes is more negative than the first predetermined delta threshold value,
   and if the time rate of change of the electrical resistance between the other pair of electrodes is neither more negative than the first predetermined delta threshold value nor more positive than the second predetermined delta threshold value,
   estimating the effective soot resistance as the previously estimated effective soot resistance modified by the time rate of change of resistance between the pair of electrodes whose time rate of change of electrical resistance is neither more negative than the first predetermined delta threshold value nor more positive than the second predetermined delta threshold value.

6. The method according to claim 2 wherein the step of determining an effective soot resistance includes the step of:
   if both the time rate of change of the electrical resistance between the first pair of electrodes and the time rate of change of the electrical resistance between the second pair of electrodes are more positive than the second predetermined delta threshold value,
   estimating the effective soot resistance as equal to the previously estimated effective soot resistance.

7. A method for determining an amount of soot accumulation on a soot sensor comprising a first pair of electrodes having a first gap therebetween and a second pair of electrodes having a second gap therebetween, the method comprising the steps of:
   determining the electrical resistance between the first pair of electrodes and the electrical resistance between the second pair of electrodes;
   determining a time rate of change of the electrical resistance between the first pair of electrodes and a time rate of change of the electrical resistance between the second pair of electrodes;
   determining an effective soot resistance based on the electrical resistance between the first pair of electrodes, the electrical resistance between the second pair of electrodes, the time rate of change of the electrical resistance between the first pair of electrodes, and the time rate of change of the electrical resistance between the second pair of electrodes;

wherein the soot sensor further comprises a controllable heater configured to effect a regeneration of the soot sensor when the heater is energized, the method further comprising the steps of:

commanding the heater to be energized in response to the electrical resistance between the first pair of electrodes being less than a first predetermined regeneration threshold value;

commanding the heater to be energized in response to the electrical resistance between the second pair of electrodes being less than a second predetermined regeneration threshold value; and commanding the heater to be energized in response to the effective soot resistance being less than a third predetermined regeneration threshold value.

8. An apparatus comprising:

a soot sensor comprising a first pair of electrodes having a first gap therebetween and a second pair of electrodes having a second gap therebetween, a processor, and a memory storing instructions that, when executed, cause the apparatus to:

determine the electrical resistance between the first pair of electrodes and the electrical resistance between the second pair of electrodes;

determine a time rate of change of the electrical resistance between the first pair of electrodes and a time rate of change of the electrical resistance between the second pair of electrodes;

determine an effective soot resistance based on the electrical resistance between the first pair of electrodes, the electrical resistance between the second pair of electrodes, the time rate of change of the electrical resistance between the first pair of electrodes, and the time rate of change of the electrical resistance between the second pair of electrodes.

9. An apparatus comprising:

a soot sensor comprising a first pair of electrodes having a first gap therebetween and a second pair of electrodes having a second gap therebetween, a processor, and a memory storing instructions that, when executed, cause the apparatus to:

determine the electrical resistance between the first pair of electrodes and the electrical resistance between the second pair of electrodes;

determine a time rate of change of the electrical resistance between the first pair of electrodes and a time rate of change of the electrical resistance between the second pair of electrodes;

determine an effective soot resistance based on the electrical resistance between the first pair of electrodes, the electrical resistance between the second pair of electrodes, the time rate of change of the electrical resistance between the first pair of electrodes, and the time rate of change of the electrical resistance between the second pair of electrodes, wherein one electrode of the first pair of electrodes and one electrode of the second pair of electrodes are electrically connected to each other to define a common electrical node on the soot sensor.

10. The apparatus of claim 9, wherein the soot sensor further comprises a resistance heater having two electrical connections thereto, wherein one of the two electrical connections to the resistance heater is electrically connected to the common electrical node on the soot sensor.

* * * * *